United States Patent
Jeong et al.

(10) Patent No.: US 11,959,131 B2
(45) Date of Patent: Apr. 16, 2024

(54) METHOD FOR MEASURING MUTATION RATE

(71) Applicant: KOREA INSTITUTE OF ORIENTAL MEDICINE, Daejeon (KR)

(72) Inventors: Sangkyun Jeong, Daejeon (KR); Soo A Oh, Daejeon (KR)

(73) Assignee: KOREA INSTITUTE OF ORIENTAL MEDICINE, Daejeon (KR)

( * ) Notice: Subject to any disclaimer, the term of this patent is extended or adjusted under 35 U.S.C. 154(b) by 970 days.

(21) Appl. No.: 16/310,236

(22) PCT Filed: Jun. 8, 2017

(86) PCT No.: PCT/KR2017/005952
§ 371 (c)(1),
(2) Date: Dec. 14, 2018

(87) PCT Pub. No.: WO2017/217694
PCT Pub. Date: Dec. 21, 2017

(65) Prior Publication Data
US 2020/0208195 A1    Jul. 2, 2020

(30) Foreign Application Priority Data

Jun. 16, 2016  (KR) .................. 10-2016-0075211
May 17, 2017  (KR) .................. 10-2017-0061225

(51) Int. Cl.
*C12Q 1/686* (2018.01)
*C12Q 1/6806* (2018.01)
(Continued)

(52) U.S. Cl.
CPC .......... *C12Q 1/686* (2013.01); *C12Q 1/6806* (2013.01); *C12Q 1/6827* (2013.01);
(Continued)

(58) Field of Classification Search
CPC ..... C12Q 1/686; C12Q 1/6806; C12Q 1/6827; C12Q 1/6869; C12Q 2549/119;
(Continued)

(56) References Cited

U.S. PATENT DOCUMENTS

| | | |
|---|---|---|
| 2013/0331279 A1 | 12/2013 | Rubin et al. |
| 2014/0227705 A1 | 8/2014 | Vogelstein et al. |
| 2015/0024950 A1 | 1/2015 | Bielas et al. |
| 2015/0275289 A1 | 10/2015 | Otwinowski et al. |
| 2018/0002747 A1* | 1/2018 | Druley ................. C12Q 1/6886 |
| 2021/0238588 A1* | 8/2021 | Fu ....................... C12Q 1/6806 |

FOREIGN PATENT DOCUMENTS

| | | |
|---|---|---|
| KR | 20140024270 | 2/2014 |
| KR | 20150143025 | 12/2015 |
| WO | WO 2012/005595 | 1/2012 |

OTHER PUBLICATIONS

Ho, T., Cardle, L., Xu, X., Bayer, M., Prince, K., Mutava, R.N., Marshall, D.F. and Syed, N., 2014. Genome-Tagged Amplification (GTA): a PCR-based method to prepare sample-tagged amplicons from hundreds of individuals for next generation sequencing. Molecular breeding, 34(3), pp. 977-988. (Year: 2014).*

(Continued)

*Primary Examiner* — Jesse P Frumkin
(74) *Attorney, Agent, or Firm* — NORTON ROSE FULBRIGHT US LLP

(57) ABSTRACT

The present invention relates to a method for measuring a mutation rate, comprising preparing a library for next generation sequencing (NGS). Accordingly, the present invention can measure the effect of drugs, radiation, gene composition, aging, and various stresses experienced by an individual, etc. on the occurrence of mutations in a subject sample, and thus can be used for testing, diagnosis, management and evaluation related to toxicity tests, medical tests, maintenance and management of health, etc.

4 Claims, 7 Drawing Sheets

Specification includes a Sequence Listing.

(51) Int. Cl.
  *C12Q 1/6827* (2018.01)
  *C12Q 1/6869* (2018.01)
  *C40B 30/00* (2006.01)
  *G06F 17/18* (2006.01)
  *G16B 20/00* (2019.01)
  *G16B 20/20* (2019.01)
  *G16B 25/00* (2019.01)
  *G16B 25/20* (2019.01)

(52) U.S. Cl.
  CPC ............ *C12Q 1/6869* (2013.01); *C40B 30/00* (2013.01); *G06F 17/18* (2013.01); *G16B 20/00* (2019.02); *G16B 20/20* (2019.02); *G16B 25/00* (2019.02); *G16B 25/20* (2019.02); *C12Q 2549/119* (2013.01)

(58) Field of Classification Search
  CPC ........ C12Q 2525/197; C12Q 2531/113; C12Q 2535/122; C12Q 2563/179; C40B 30/00; G06F 17/18; G16B 20/00; G16B 20/20; G16B 25/00; G16B 25/20; G16B 20/50; G16B 30/10; G16B 30/00
  See application file for complete search history.

(56) References Cited

OTHER PUBLICATIONS

Jeong, SK. Mar. 25, 2022 Google machine translation of KR10-2016-0075211. 37 pages. (Year: 2016).*
International Search Report and Written Opinion issued in corresponding application No. PCT/KR2017/005952, dated Dec. 7, 2017 (English translation provided).
Lee et al., "PNA-Mediated PCR Clamping for the Detection of EGFR Mutations in Non-Small Cell Lung Cancer" *Tuberc Respir Dis.* 2010, 69, 271-278 (English Abstract).
Extended European Search Report issued in corresponding application No. 17813518.2, dated Dec. 18, 2019.
Ford et al., "Use of whole genome sequencing to estimate the mutation rate of *Mycobacterium tuberculosis* during latent infection" Nature Genetics 2011, 43(5), 7 pages.
Keightley et al., "Analysis of the genome sequences of three *Drosophila melanogaster* spontaneous mutation accumulation lines" Genome Research 2009, 19, 1195-1201.
Roach et al., "Analysis of Genetic Inheritance in a Family Quartet by Whole-Genome Sequencing" Science 2010, 328, 636-639.

* cited by examiner

[FIG. 3a]
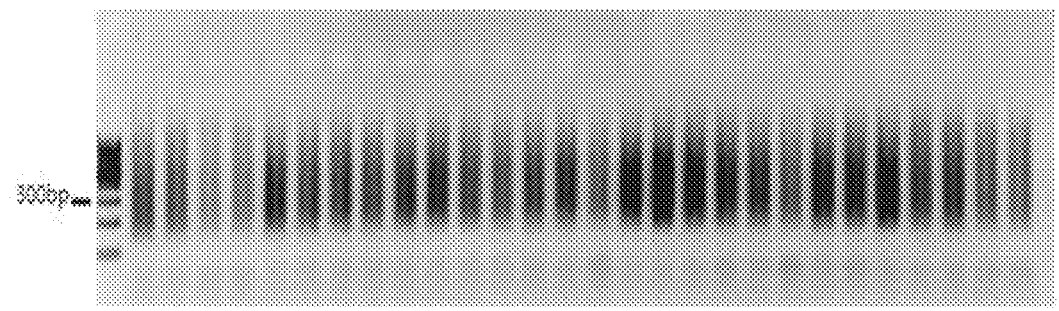
[FIG. 3b]
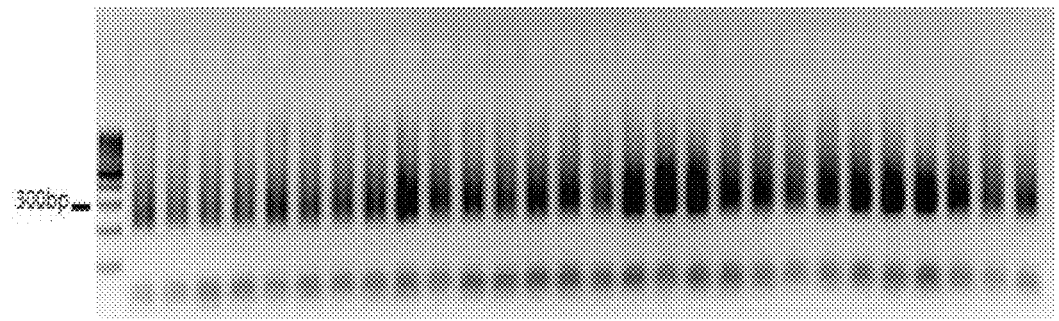

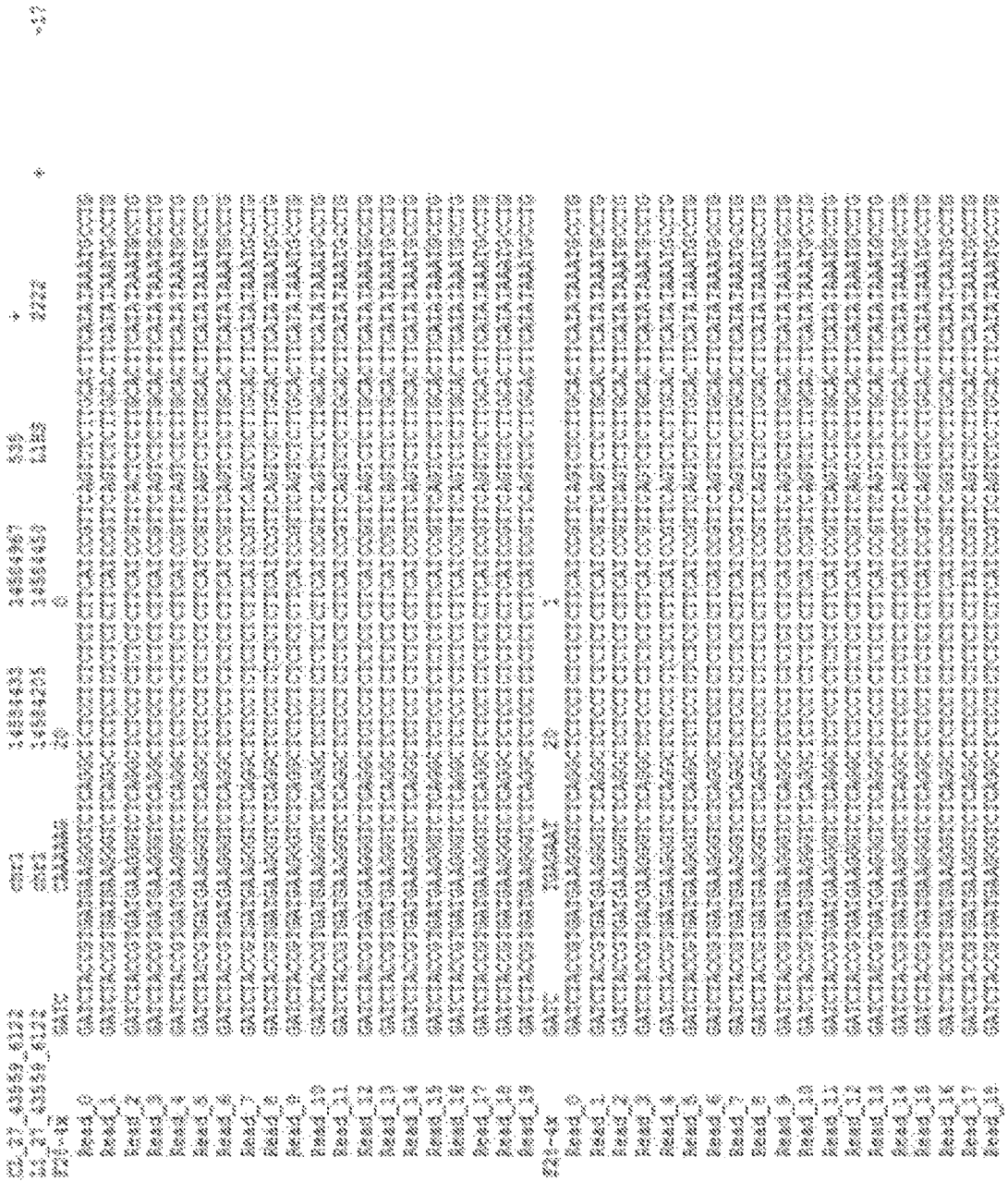
[FIG. 4]

[FIG. 5]

METHOD FOR MEASURING MUTATION RATE

SEQUENCE LISTING

The instant application contains a Sequence Listing which has been filed electronically in ASCII format and is hereby incorporated by reference in its entirety. Said ASCII copy, created on Oct. 31, 2019, is named HANO_P0021US_1001055501_SL.txt and is 13,796 bytes in size.

TECHNICAL FIELD

The present invention relates to a method for measuring a mutation rate, including preparing a library for next-generation sequencing (NGS).

BACKGROUND ART

Mutations are one of the most notable areas in various fields of the life sciences, such as the prediction of diseases, etc. In particular, as the world is rapidly becoming an aged society, there is a growing interest in health. Therefore, studies on the measurement of mutation rates have been actively carried out so as to increase the predictability of diseases for improving the quality of life.

Meanwhile, Korean Laid-Open Patent Publication No. 2015-0143025 discloses methods for detecting mutations of filaggrin gene using PNAs (peptide nucleic acids) as a technique for detecting mutations. In addition, studies using PNAs for detecting mutations in the epidermal growth factor receptor (EGFR) have been continuously reported (Tuberc Respir Dis 2010; 69:271-278).

However, PNAs cannot be produced naturally, but can only be made synthetically; thus, they are very costly and have limitations in that they cannot be easily used in the measurement of large-scale mutation rates. Further, the methods for detecting mutations using PNAs can only detect mutations of a specific gene and have limitations in detecting randomly occurring mutations. Therefore, various studies for the measurement of mutation rates are still required.

DISCLOSURE

Technical Problem

Accordingly, the present inventors have made extensive efforts to develop a method for measuring a mutation rate with high accuracy, while enabling the measurement of large-scale mutation rates, and have developed a method for measuring a mutation rate capable of extensively measuring the rate of randomly-occurring mutations with improved accuracy, including analyzing a nucleotide sequence by amplifying a random sequence and a target sequence introduced with an adapter, thereby completing the present invention.

In addition, the present invention employs different genetic materials and thus can measure variants included in the genetic materials, and can also provide a more accurate measurement value since distortions caused by various types of noise introduced during the experimentation are removed due to the properties of the invention. For example, it can be used to measure the content and extent of heteroplasmy in mitochondrial DNA or to measure the ecological structure of microorganisms from microbial genomes.

Technical Solution

The main object of the present invention is to provide a method for measuring a mutation rate of a genome, comprising the following steps (1) to (7):

(1) preparing a library for next-generation sequencing (NGS), comprising the following steps (a) to (c):
  (a) preparing a DNA-adapter ligates by cleaving each genomic DNA having landmark sequences extracted from an individual with a restriction enzyme and joining the adapter comprising a part of random sequences that distinguishes one adaptor molecule from another to both ends of each cleaved genomic DNA:
  (b) obtaining an amplification product by using the DNA-adapter ligates prepared in step (a) as a template and performing PCR using a first primer, which binds to the 3' end of the landmark sequences, and a second primer, which binds to the 5' end of the adapter; and
  (c) performing PCR by using the amplification product prepared in step (b) as a template, and a primer pair which binds to both ends of the template;
(2) determining the sequence of each genome fragment included in the library through NGS;
(3) grouping the amplification products into a number of n by aligning the amplification products prepared in step (c) based on n number of landmarks on a reference genome sequence;
(4) selecting $m_i$ number of genome fragments for each group (wherein $m_i$ is the number of genome fragments selected in the $i^{th}$ landmark) by sub-grouping the amplification products constituting the group according to the random sequences, then selecting one genome fragment for each $m_i$ number of sub-groups;
(5) determining one representative nucleotide sequence without mutations for each group by comparing the nucleotide sequences of $m_i$ number of genome fragments;
(6) determining a total number (M) of mutations by judging a case where a genome fragment having a nucleotide sequence different from the representative nucleotide sequence of each group among the $m_i$ number of genome fragments of n number of groups as a mutation; and
(7) calculating an accumulated mutation rate (AMR) using the following Calculation Equation 1.

Advantageous Effects

The present invention can accurately measure the size of analyzed genome fragments and the mutation rate by amplifying the selectively captured genome fragments from a subject sample for analysis such that the template can be distinguished, and comparing the nucleotide sequences of the respective templates. Through the method, the effect of environmental changes, such as drugs, radiation, gene composition, aging, and various stresses experienced by an individual, etc., on the occurrence of mutations in a subject sample can be measured, and thus the method can be used for testing, diagnosis, management, and evaluation related to toxicity tests, medical tests, maintenance and management of health, etc.

BRIEF DESCRIPTION OF DRAWINGS

FIG. 3a is a diagram showing the result of electrophoresis on 2% agarose gel after amplifying the genome fragments.

FIG. 3b is a diagram showing the result of electrophoresis of the DNA sequence library of the genome fragments on 2% agarose gel.

FIG. 4 discloses SEQ ID NOS 13-32, 13-14, 33, 16-28, 34-35, and 31, respectively, in order of appearance. The diagram shows the result of sequencing obtained through NGS.

FIG. 5 discloses SEQ ID NOS 36-47, respectively, in order of appearance. The diagram shows the genome fragments having one different nucleotide sequence as a result of sequencing of the genome fragments.

BEST MODE

Figure 1:
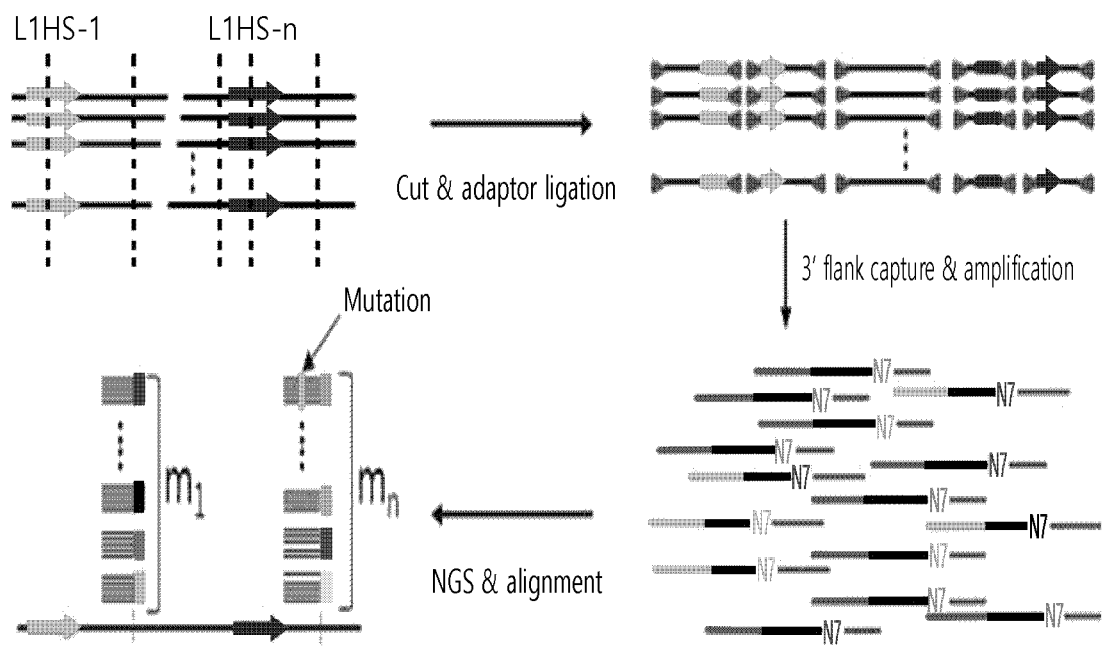
FIG. 1 is a schematic diagram showing the method for measuring a mutation rate from a sample.

In order to achieve the object above, one aspect of the present invention provides a method for measuring a mutation rate of a genome, comprising the following steps (1) to (7):

(1) preparing a library for next-generation sequencing (NGS), comprising the following steps (a) to (c):
  (a) preparing a DNA-adapter ligates by cleaving each genomic DNA having landmark sequences extracted from an individual with a restriction enzyme and joining the adapter comprising a part of random sequences that distinguishes one adaptor molecule from another to both ends of each cleaved genomic DNA;
  (b) obtaining an amplification product by using the DNA-adapter ligates prepared in step (a) as a template and performing PCR using a first primer, which binds to the 3' end of the landmark sequences, and a second primer, which binds to the 5' end of the adapter; and
  (c) performing PCR by using the amplification product prepared in step (b) as a template and a primer pair which binds to both ends of the template;

(2) determining the sequence of each genome fragment included in the library through NGS;

(3) grouping the amplification products into a number of n by aligning the amplification products prepared in step (c) based on n number of landmarks on a reference genome sequence;

(4) selecting $m_i$ number of genome fragments for each group (wherein $m_i$ is the number of genome fragments selected in the $i^{th}$ landmark) by sub-grouping the amplification products constituting the group according to the random sequences, then selecting one genome fragment for each $m_i$ number of sub-groups:

(5) determining one representative nucleotide sequence without mutations for each group by comparing the nucleotide sequences of $m_i$ number of genome fragments;

(6) determining a total number (M) of mutations by judging a case where a genome fragment having a nucleotide sequence different from the representative nucleotide sequence of each group among the $m_i$ number of genome fragments of n number of groups as a mutation; and (7) calculating an accumulated mutation rate (AMR) using the following Calculation Equation 1.

$$AMR = \frac{M}{\sum_{1}^{n} m_i \times l_i} \quad \text{[Calculation Equation 1]}$$

(wherein AMR represents accumulated mutation rate; M represents the total number of mutations; $m_i$ represents the number of genome fragments selected in the $i^{th}$ landmark; $l_i$ represents the number of nucleotides whose sequences are determined and analyzed among the genome fragments of the $i^{th}$ landmark).

Step 1 provides a step of preparing a library for next-generation sequencing, comprising steps (a) to (c).

As used herein, the term "next-generation sequencing (NGS)" is a high-speed analysis method for the nucleotide sequences of a genome, and can be used interchangeably with high-throughput sequencing, massive parallel sequencing, or second-generation sequencing.

As used herein, the term "library" refers to a set of fragments of a gene obtained by cleavage with restriction enzymes, etc., and may be, but is not limited to, a set of fragments of a gene introduced into a vector. Specifically, in the present invention, the library may be prepared through the following steps (a) to (c), and the library may be used to measure the mutation rate.

Step (a) provides a step of preparing a DNA-adapter ligates by cleaving each genomic DNA having landmarks extracted from an individual with a restriction enzyme and joining the adapter comprising a part of random sequences that distinguishes one adaptor molecule from another to both ends of each cleaved genomic DNA.

As used herein, the term "individual" may refer to any animal, including humans, that requires the measurement of a mutation rate.

Any method used in the art may be used as the method for extracting the genomic DNA from an individual without limitation.

The term "landmark" refers to a specific nucleotide sequence to be distinguished from other nucleotide sequences in the genomic DNA. In one example, it may be a specific nucleotide sequence repeated in the genomic DNA. Specifically, it may be a LINE (long interspersed nuclear element)- or SINE (short interspersed nuclear element)-based repeating nucleotide sequence, or a nucleotide sequence repeated within the genome such as a specific restriction enzyme recognition site, but is not limited thereto. In addition, any nucleotide sequence capable of measuring a mutation rate of a specific region by being distinguished from other nucleotide sequences can be used without limitation.

In one embodiment of the present invention, L1HS nucleotide sequence, which is a LINE-based repeating sequence, was used as a landmark for measuring the mutation rate.

As used herein, the term "adapter" refers to a nucleotide sequence of a partial double-stranded structure used to obtain an amplification product containing all or part of a landmark and a nucleotide sequence of a restriction enzyme cleavage site, and it can bind to both ends of genomic DNA cleaved by a restriction enzyme. Specifically, the adapter may include a random sequence.

One end of the adapter may include a sequence which complementarily binds to a genomic DNA region cleaved by a restriction enzyme.

In addition, the adapter may include a nucleotide sequence capable of attaching a primer at the time of performing PCR in the step of preparing an amplification product for measuring the mutation rate.

In one embodiment of the present invention, the genomic DNA of human white blood cells was cleaved with a DpnII restriction enzyme, and a DpnII adapter including a random sequence capable of binding to the cleavage site of the restriction enzyme was attached to the cleaved genomic DNA.

Meanwhile, the adapter of the present invention may be one in which a phosphate group is bound at the 5' region to capture all of the complementary strands of the landmark DNA. In addition, in order to distinguish the complementary DNA strand, it may include one or more mismatch nucleotides in the double-stranded region of the adapter.

That is, when only one strand of the landmark DNA is captured, it may be difficult to distinguish false positives caused by a chemical mutation occurring in a reaction, such as the library construction step, etc., and such a chemical mutation cannot occur at the same position of the complementary strands of DNA at the same time. Thus, by using the adapter capable of capturing both strands of the landmark DNA, it is possible to remove the noise caused by the chemical mutation and to measure the mutation rate more accurately.

In addition, a restriction enzyme that produces non-palindrome overhangs can be used to prevent binding between the adapters. The restriction enzyme may be, but is not limited to, BstNI or AvaII restriction enzyme.

As used herein, the term "random sequence" refers to any 5 to 11 nucleotides used to distinguish the origin of genomic DNA extracted from an individual, and may include a specific nucleotide sequence. The random sequence may bind to both ends of the genomic DNA cleaved by a restriction enzyme. Further, it shows a different nucleotide sequence for each genomic DNA origin, and thus, the mutation rate according to the respective origin of the genomic DNA may be easily measured when measuring the mutation rate from an amplification product. The random sequence may be located in a single strand part of the partial double-stranded structure of the adapter, but is not limited thereto.

In one embodiment of the present invention, any seven nucleotides were used as a random sequence.

As used herein, the term "DNA-adapter ligates" refers to a construct in which the genomic DNA cleaved by the restriction enzyme and the adapter are ligated, and is used as a template for amplification in order to measure the mutation rate. Specifically, the ligates may include a random sequence, for example the random sequence may be located between the genomic DNA and the adapter.

Step (b) provides a step (b-1) of obtaining an amplification product by using the DNA-adapter ligates prepared in step (a) as a template and performing PCR using a first primer, which binds to the 3' end of the landmark, and a second primer, which binds to the 5' end of the adapter.

The first primer is a primer that binds to the 3' end of the landmark, and the second primer is a primer that binds to the 5' end of the adapter. When performing PCR using the primers, the primers serve to capture the nucleotide sequence downstream to the 3' region of the landmark.

As used herein, the term "amplification product" refers to a product of PCR performed using a first primer and a second primer, and may include a landmark, a random sequence, a genome fragment, and an adapter. Specifically, the amplification product may include all or part of the sequence of the landmark, and may include all or part of the sequence of the adapter, but is not limited thereto.

As used herein, the term "genome fragment" is a sequences including the genomic DNA as a target for the measurement of the mutation rate, and can bind to a landmark and a random sequence to be distinguished from other genomic DNAs. Specifically, the genome fragment may include at least one nucleotide, and may include all or part of the genomic DNA cleavage site by the restriction enzyme in step (a).

In one embodiment, amplification products were obtained by using the DNA-adapter ligates including the genomic DNA cleaved by the restriction enzyme, the random sequence and the adapter, and performing PCR using a first primer, which binds to the 3' end of the L1HS landmark, and a second primer, which binds to the 5' end of the adapter.

Step (b) may further include a step (b-2) of performing nested PCR by using the amplification product prepared above as a template and using a forward primer, which binds to all or part of the nucleotide sequence of the landmark, and a reverse primer, which binds to all or part of the adapter except for the random sequence.

As used herein, the term "nested PCR" refers to PCR for removing undesired amplification products using a first PCR amplification product as a template and specifically selecting only desired amplification products. Since the nested PCR can remove undesired amplification products, it can exhibit an effect of improving accuracy at the time of measuring the mutation rate in the present invention.

In order to perform the nested PCR for removing undesired amplification products, the primers which bind to each of the landmark and the adapter for capturing a genome fragment can be used. Specifically, one of the primers may bind to all or part of the nucleotide sequence of the landmark, and the other primer may bind to all or part of the nucleotide sequence of the adapter.

Further, the primers may be primers having additional nucleotide sequences suitable for next-generation sequencing, but are not limited thereto.

Step (c) provides a step of performing PCR by using the amplification product prepared in step (b) as a template and a primer pair which binds to both ends of the template.

The primer pair of step (c) may bind to both ends of the amplification product prepared in step (b). The primer pair may consist of a first primer, and a second primer including a different index for each template, and thus can be used to distinguish the library of the amplification products. Specifically, the different index for each template may be a conventional index that is generally used in next-generation sequencing. In addition, the primer pair may be a primer pair having additional nucleotide sequences suitable for next-generation sequencing.

Figure 2:
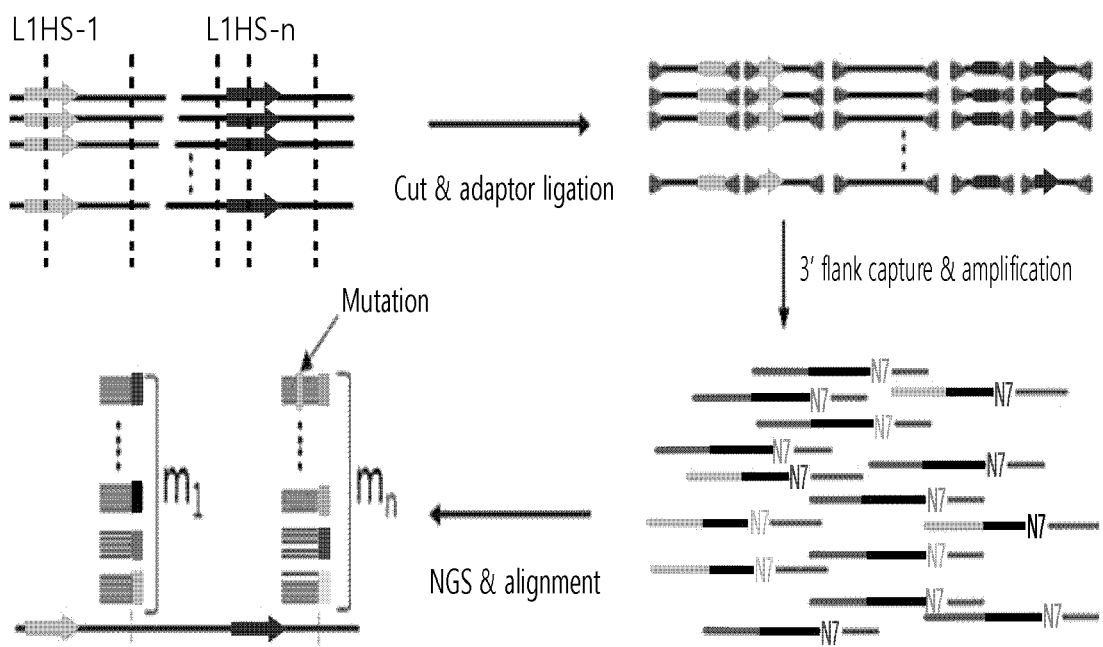
FIG. 2 discloses SEQ ID NOS 7, 5, 3, 10-12, 1, 4, 6, and 8, respectively, in order of appearance. The diagram shows the template used for constructing a DNA sequence library of a genome fragment including a random sequence and an adapter, and the types of primers.

In one embodiment of the present invention, a library for NGS was prepared by using the primer pair including nucleotide sequences suitable for next-generation sequencing (FIG. 2).

Step 2 provides a step of determining the sequence of each genome fragment constituting the library through NGS.

The terms "genome fragment" and "NGS" are the same as described above.

The sequences of the genome fragments can be analyzed using a sequencer used for next-generation sequencing, and any sequencer can be used without limitation as long as it is a device commonly used in next-generation sequencing.

The library may have additional nucleotide sequences suitable for next-generation sequencing added through step (c), and thus can be easily used in next-generation sequencing.

Step 3 provides a step of grouping the amplification products into a number of n by aligning the amplification products prepared in step (c) based on n number of landmarks on a standard genome sequence.

Specifically, step 3 is a step of aligning the amplification products prepared in step (c) including the genomic DNA isolated from an individual on the reference genome sequence, wherein the alignment of the amplification products is carried out by aligning the products based on one or more landmarks and grouping into the number of landmarks.

As used herein, the term "reference genomic sequence" refers to a general or average genomic sequence of a specific individual, and refers to a nucleotide sequence of a genome to be used as a reference when comparing various types of genetic factors, etc. of individual genomic sequences. In the present invention, the reference genomic sequence employs the same nucleotide sequence of an individual as that of the genome fragment, which is a target for the measurement of the mutation rate, and thus can be easily used in the measurement of the mutation rate for each landmark, as the landmarks between the reference genomic sequence and the genome fragment are identical.

Step 4 provides a step of selecting $m_i$ number of genome fragments for each group by sub-grouping the amplification products constituting the group according to the random sequences, then selecting one genome fragment for each $m_i$ number of sub-groups, wherein $m_i$ is the number of genome fragments selected in the $i^{th}$ landmark.

Specifically, in step 4, the $m_i$ number of genome fragments may be selected for each group by sub-grouping the amplification products according to the random sequences in each group, which is grouped in step 3, followed by selecting one genome fragment for each sub-group.

When one genome fragment is selected for each sub-group, it is possible to select genome fragments having the same sequences as the matching nucleotide sequences of the sub-grouped amplification products according to each random sequence, and when one genome fragment in the same random sequence is supported by 5 or more of the amplification products, the selected genome fragments may be considered valid.

Step 5 provides a step of determining one representative nucleotide sequence without mutations for each group by comparing the nucleotide sequences between the $m_i$ number of genome fragments, and step 6 provides a step of determining a total number (M) of mutations by judging a case where a genome fragment having a nucleotide sequence different from the representative nucleotide sequence of each group among the $m_i$ number of genome fragments of n number of groups as a mutation.

Specifically, a representative nucleotide sequence without mutations can be determined by aligning the nucleotide sequences of the $m_i$ number of genomic fragments, which are distinguished by different random sequences, while belonging to the same landmark, and the representative nucleotide sequence and the sequences of the genome fragments can be compared. In a case where there are 10 or more genome fragments having different random sequences arranged in the same landmark, when there is one genome fragment having a different nucleotide, it is classified as a mutation, and when there are two or more genome fragments, it is classified as a polymorphism, and accordingly, the total number of mutations can be determined.

Step 7 provides a step of calculating an accumulated mutation rate (AMR) using the following Calculation Equation 1.

$$AMR = \frac{M}{\sum_{1}^{n} m_i \times l_i}$$ [Calculation Equation 1]

In the Calculation Equation 1, AMR represents accumulated mutation rate, M represents the total number of mutations; $m_i$ represents the number of genome fragments selected in the $i^{th}$ landmark; and $l_i$ represents the number of nucleotides whose sequences are determined and analyzed among the genome fragments of the $i^{th}$ landmark.

Figure 6:
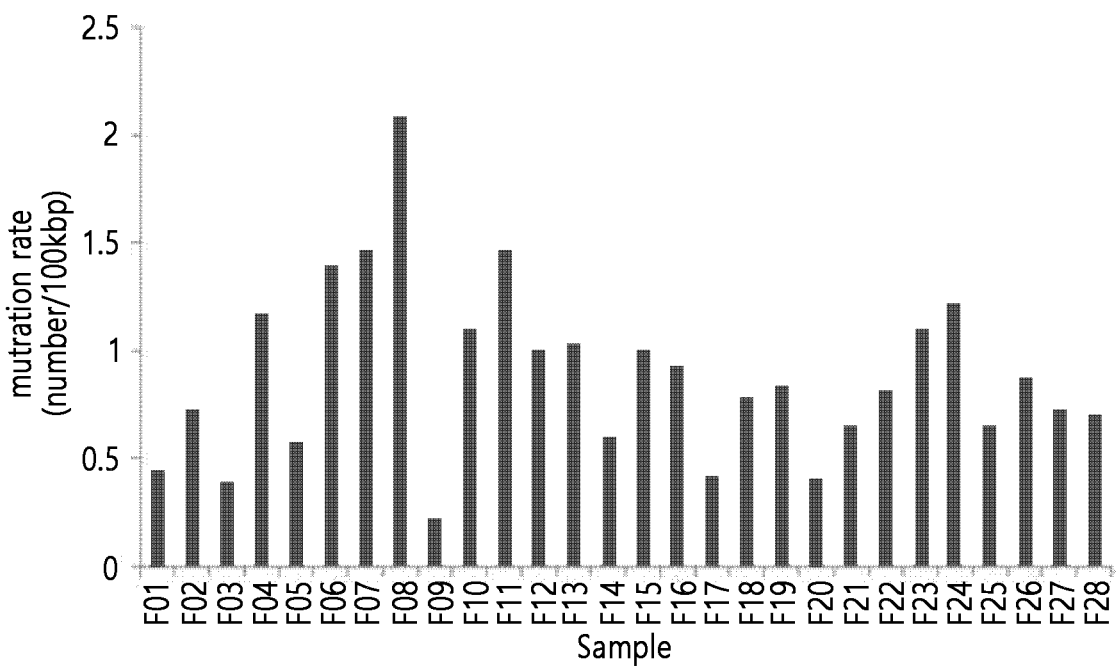
FIG. 6 is a graph showing the measurement result of mutation rates for 28 samples.

In one embodiment of the present invention, the total number of mutations was determined from 28 samples of human white blood cells through steps (1) to (6), and the mutation rate was calculated using Calculation Equation 1 above. As a result, it was confirmed that in the 28 samples, 0.2 to 2.1 mutations were found in every 10,000 nucleotides, and an average of 0.9 mutations occurred therein (FIG. 6).

MODE FOR INVENTION

Hereinafter, the action and effect of the present invention will be described by way of Examples. However, these Examples are provided for illustrative purposes only, and the scope of the invention is not intended to be limited by these Examples.

Example 1: Construction of DNA Sequence Library of Genome Fragments 28 samples of genomic DNA of human w % bite blood cells deposited under KDC (Korean medicine Data Centre) were obtained from the Korea Institute of Oriental Medicine, and a DNA sequence library of the genome fragments was constructed in the same manner as in FIG. 1.

Specifically, 200 ng of genomic DNA for each sample was cleaved by DpnII restriction enzyme at 37° C. for 2 hours and then purified with a PCR purification kit and dissolved in 30 μL of elution buffer, 50 ng of each cleaved genomic DNA and 16 pmol of an adapter, which is a hybridized partially double-stranded DNA of SEQ ID NO: (5'-3': GAGCAGGTGACTCTGGCTTCCTA-CACGACGCTCTTCCGATCTNNNNNNNCACCCACA CTTGACC) including a random sequence and SEQ ID NO: 2 (5'-3': AATTGGTCAAGTGTGGGTG), which forms an overhang capable of binding to the DpnII cleavage site by complementary binding to the 3' end of SEQ ID NO: 1, were mixed in an aqueous solution containing 400 U of DNA ligase (Solgent) and 1× buffer, and reacted at room temperature for 1 hour. The adapter was attached to the cleavage site obtained by the restriction enzyme through the above reaction, purified with a PCR purification kit, and dissolved in 30 μL of elution buffer. 1 μL, 2 μL, and 4 μL of each DNA to which the adapter was attached was taken to be used as a template for PCR reaction, and PCR was carried out using an L1_C primer of SEQ ID NO: 3, which binds to the 3' region of L1HS, and an A_C primer of SEQ ID NO: 4, which binds to the 5' region based on the adapter, under the conditions shown in Table 1 below. At this time, the extension reaction of the 3' region performed at 68° C. for 10 minutes is a step for filling the single strand region of the adapter so that both strands can be used as a template for the amplification reaction in the subsequent PCR reaction, and it may be carried out as an independent reaction by using another DNA polymerase.

Meanwhile, the primers are as shown in Table 2.

TABLE 1

| Temperature (° C.) | Time | Note |
| --- | --- | --- |
| 68 | 10 min | 3' extension reaction |
| 95 (denaturation) | 20 sec | Repeated for 20 cycles |
| 58 (annealing) | 20 sec | |
| 68 (extension) | 2 min | |
| 68 | 8 min | |

TABLE 2

| Types of primers | Nucleotide sequence (5'-3') |
| --- | --- |
| L1_C primer | GGGAGATATACCTAATGCTAGATGACAC (SEQ ID NO: 3) |
| A_C Primer | GAGCAGGTGACTCTGGCTT (SEQ ID NO: 4) |

1 μL of the amplification product of the genome fragment obtained as a result of the PCR was taken to be used as a template for the subsequent nested PCR, and the nested PCR was carried out using an L1_N primer of SEQ ID NO: 5, which binds to the 5' end of the amplification product, and an A_N primer of SEQ ID NO: 6, which binds to the 3' end, under the same conditions as shown in Table 1. A sequence library for NGS was constructed using an NGS_F primer of SEQ ID NO: 7 and an NGS_R primer of SEQ ID NO: 8 under the same conditions as shown in Table 1 by taking 0.1 μL of the amplification product obtained as a result of the nested PCR and attaching nucleotide sequences necessary for NGS (next-generation sequencing) to both ends of the amplification product (FIG. 2). At this time, the primers having a different index for the NGS_F primer were used for each library in order to distinguish the library of the amplification product. Meanwhile, the primers are shown in Table 3.

The amplification product and the constructed library were subjected to electrophoresis on 2% agarose gel. As a result, it was confirmed that they showed similar patterns, thereby confirming that it was possible to construct the library for properly measuring the mutation rate through the above method (FIGS. 3a and 3b).

TABLE 3

| Types of primers | Nucleotide sequence (5'-3') |
| --- | --- |
| L1_N primer | GTGACTGGAGTTCAGACGTGTGCTCTTCCGATCTTGCACATGTACCCTAAAACTTAG (SEQ ID NO: 5) |
| A_N primer | CTACACGACGCTCTTCCGAT (SEQ ID NO: 6) |
| NGS_F primer | CAAGCAGAAGACGGCATACGAGATCGTGATGTGACTGGAGTTCAGACGTGTG (SEQ ID NO: 7) |
| NGS_R primer | AATGATACGGCGACCACCGAGATCTACACTCTTTCCCTACACGACGCTCTTCCGATCT (SEQ ID NO: 8) |

Example 2: NGS Measurement of Mutation Rate Through Data Analysis

The nucleotide sequence of the amplification products of the library constructed in Example 1 was determined using a sequencer (HiSeq2000, Illumina). Among the sequences of amplification products, those contained no ambiguous nucleotide sequences and carry the nucleotide sequence necessary for NGS were selected, and then they were aligned to the reference genome sequence, independently arranged in the L1HS landmark, and grouped.

The random sequences, which were used as a molecular index of the amplified products arranged in each landmark, were extracted and sub-grouped according to each template from which they were derived. Subsequently, the originated matching nucleotide sequences of the sub-grouped genome fragments were determined, and the genome fragments having the nucleotide sequences were selected. At this time, the matching nucleotide sequences were considered valid w % ben there were five or more amplification products in one random sequence.

As a result of the sub-grouping, as an example, there were a total of 43,559 amplification products having the DNA of the F28 sample as an example, and they had 6,122 random sequences. In addition, the amplification products grouped in the 27$^{th}$ landmark of the L1HS among the amplification products were arranged on a positive strand having a size of 535 bp, ranging from 14584433 to 14584967 on the 1$^{st}$ chromosome, and was found to be −17 bp away from L1HS having a size of 2,222 bp. Meanwhile, among random sequences as represented with numbers from 0 to 20, the first random sequence represented by 0 consisted of the sequence 'CAAAAAG', and there were 20 sequence reads (Read_0 to Read_19) sub-grouped according to the random sequence. Further, the second random sequence represented by 1 consisted of the sequence 'TGAGAAT', and it was confirmed that there were 19 sequence reads (Read_0 to Read 18) sub-grouped according to the random sequences (FIG. 4).

Figure 5:
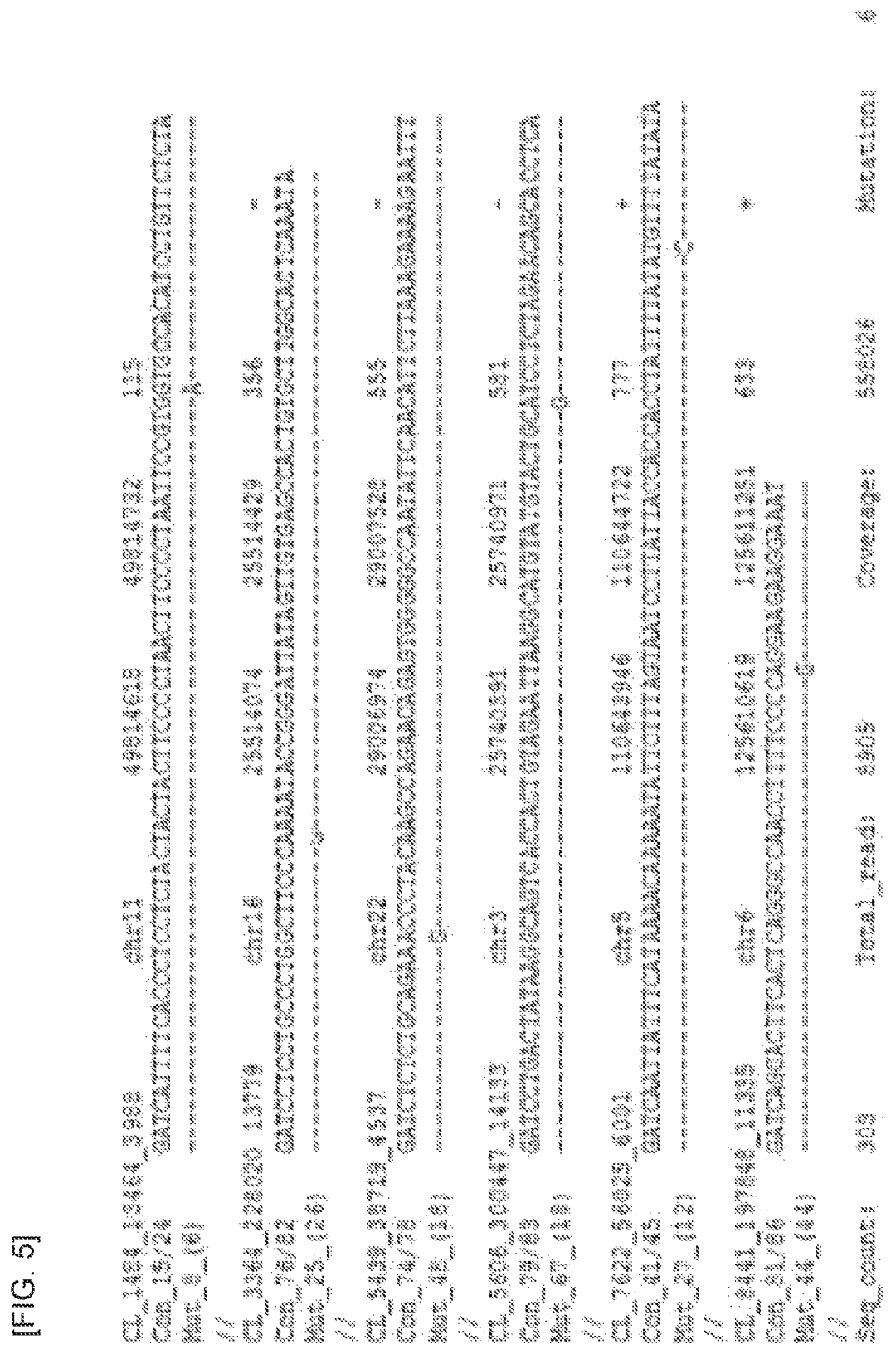

Meanwhile, the nucleotide sequences of the genome fragments defined by different random sequences while belonging to the same landmark were aligned with each other to determine a representative nucleotide sequence without mutations, and then this was compared with the nucleotide sequences of the genome fragments selected above. Specifically, in a case where there were 10 or more genome fragments having different random sequences arranged in the same landmark, when there was one genome fragment having a different nucleotide sequence, it was classified as a mutation, and when two or more genome fragments were present, this was classified as a polymorphism. As a result, as one example, the amplification products (CL_1484) grouped in the 1.484$^{th}$ landmark of the L1HS were arranged in a negative strand having a size of 115 bp, ranging from 49814618 to 49814732 on the 11$^{th}$ chromosome. The mutations occurred in a specific genome fragment among the sub-grouped genome fragments of the amplification products, and specifically, it was confirmed that the position of the specific nucleotide in which the mutations occurred could be found. Furthermore, it was confirmed that mutations occurred in 6 nucleotides among 558,026 nucleotides in a total of 8,905 amplification products (FIG. 5).

Meanwhile, as a result of the detailed analysis of the amplification products grouped in the 1,484$^{th}$ landmark of L1HS, it was confirmed that 15 nucleotide sequences among the nucleotide sequences of the genome fragments distinguished by 24 random sequences coincided with the representative nucleotide sequence (Con_15/24). In addition, it was confirmed that the mutation occurred in the 8$^{th}$ random sequence consisting of 6 amplification products, and the remaining nucleotide sequences were excluded from the analysis because either the number of amplification products did not reach 5, or some of the amplification products were inconsistent with the representative nucleotide sequence (FIG. 5).

The mutation rate was calculated using the following Calculation Equation 1 by calculating the number of genome fragments having different random sequences according to the analyzed landmarks, the total number of nucleotides included in the nucleotide sequences, and the total number of mutation events.

$$AMR = \frac{M}{\sum_{1}^{n} m_i \times l_i} \quad \text{[Calculation Equation 1]}$$

(wherein AMR represents accumulated mutation rate; M represents the total number of mutations; $m_i$ represents the number of genome fragments selected in the $i^{th}$ landmark; $l_i$ represents the number of nucleotides whose sequences are determined and analyzed among the genome fragments of the $i^{th}$ landmark)

As a result, it was confirmed that in the 28 samples, the mutation rate showed a distribution of 0.2 to 2.1 mutations in every 10,000 nucleotides and had an average of 0.9 mutations (FIG. 6). Therefore, it was confirmed that the size of the analyzed DNA and the number of mutations could be accurately determined by the method for measuring the mutation rate of the present invention.

Figure 7:
FIG. 7 is a diagram showing an adapter prepared by modifying the adapter prepared in Example 1.

Example 3: Confirmation of Improvement of Accuracy on Measurement of Mutation Rate Using Modified Adapter The genomic DNA used in Example 1 was cleaved by AvaII restriction enzyme at 37° C. for 2 hours, and then purified in the same manner as in Example 1 and dissolved in the elution buffer. The cleaved genomic DNA was attached to the complementary binding site of the adapter through the same conditions and procedures as in Example 1, using the adapter in which the nucleotide sequence of SEQ ID NO: 1 and SEQ ID NO: 9 (5'-3': GTCGGT-CAAGTGTGGGTG) were complementarily bound such that the adapter could be attached to captured DNA by a ligation reaction since it includes one mismatched base pair and a phosphate bound to the 5' end, and that the AvaII restriction enzyme cleavage site was formed, and the resultant was purified and dissolved in the elution buffer (FIG. 7).

Using the same conditions and procedures as in Example 1, the DNA to which the adapter was attached was subjected to PCR amplification, and the library for NGS was constructed. As for the prepared library, the nucleotide sequences were determined and analyzed through the same process and procedure as in Example 2. The nucleotide sequences having the same random sequences were enumerated according to each landmark so as to identify the mismatched regions on nucleotide sequences 1 and 2 of the adapter, thereby confirming the complementary relationship of the double helix.

Therefore, it was confirmed that by using the adapter modified as described above, only those mutations whose nucleotide sequences of the captured DNA having a mutually complementary relationship matched were selected as effective mutations, and thus, various mutations occurring in only one strand of the double helix could be distinguished during experimentation. As a result, it is confirmed that distortions caused by various types of noise generated during the experimentation were eliminated, thereby providing more accurate measurement values.

While the present disclosure has been described with reference to the particular illustrative embodiments, it will be understood by those skilled in the art to which the present disclosure pertains that the present disclosure may be embodied in other specific forms without departing from the technical spirit or essential characteristics of the present disclosure. Therefore, the embodiments described above are considered to be illustrative in all respects and not restrictive. Furthermore, the scope of the present disclosure is defined by the appended claims rather than the detailed description, and it should be understood that all modifications or variations derived from the meanings and scope of the present disclosure and equivalents thereof are included in the scope of the appended claims.

The invention claimed is:

1. A method of identifying mutation, the method comprising the following steps (1) to (6):
   (1) preparing a library of genome fragments for next generation sequencing (NGS), comprising the following steps (a) to (c):
      (a) preparing DNA-adaptor ligates for a plurality of genomic DNA by:
         (i) cleaving each genomic DNA with a restriction enzyme; and
         (ii) joining adaptors to both ends of each cleaved genomic DNA, each adaptor comprising at least a random sequence that distinguishes each adaptor molecule from another by genomic DNA origin, wherein each end of a cleavage site of the genomic DNA is joined by at least one adaptor;
      (b) obtaining amplification products by using the DNA-adaptor ligates prepared in step (a) as templates and performing a polymerase chain reaction (PCR) using a primer that binds to the 3' end of a nucleotide sequence of interest at a specific region of genomic DNA and a primer that binds to the 5' end of the adaptors;
      (b-2) using the amplification products of step (b) as a template and performing nested PCR using:
         (i) a forward primer that binds to all or part of a nucleotide sequence of the specific region of genomic DNA; and
         (ii) a reverse primer that binds to all or part of the adaptor except for the random sequences, to produce nested amplification products, and
      (c) performing a second PCR by using the nested amplification products prepared in step (b-2) as templates and a primer pair which binds to both ends of the templates to form genome fragments;
   (2) determining the sequence of each genome fragment included in the library through NGS;
   (3) grouping the amplification products into a number of n by aligning the amplification products prepared in step (c) based on n number of landmarks on a reference genome sequence;
   (4) selecting $m_i$ number of genome fragments for each group, wherein $m_i$ is the number of genome fragments selected in the ith landmark, by sub-grouping the amplification products constituting the group according to the random sequences, then selecting one genome fragment for each $m_i$ number of sub-groups;
   (5) determining one representative nucleotide sequence without mutations for each group by comparing the nucleotide sequences of $m_i$ number of genome fragments; and
   (6) determining a mutation when there is a nucleotide sequence different from the representative nucleotide sequence of each group among the $m_i$ genomic fragments of n groups.

2. The method of claim 1, wherein, in step (c), the primer pair consists of a first primer and a second primer, in which the second primer comprises a different molecular index for each template.

3. The method of claim 1, further comprising verifying an accumulated mutation rate (AMR) using the following Equation 1:

$$AMR = \frac{M}{\sum_{1}^{n} m_i \times l_i} \qquad [\text{Equation 1}]$$

wherein AMR represents accumulated mutation rate; wherein M represents the total number of mutations; $m_i$ represents the number of genome fragments selected in the ith landmark; $l_i$ represents the number of nucleotides whose sequences are determined and analyzed among the genome fragments of the ith landmark.

4. The method of claim 1, wherein, in step (6), if there is one genome fragment having a different nucleotide at the same position when $m_i$ is 10 or more, the nucleotide is regarded as a mutation.

* * * * *

SEQUENCE LISTING

```
<160> NUMBER OF SEQ ID NOS: 48

<210> SEQ ID NO 1
<211> LENGTH: 64
<212> TYPE: DNA
<213> ORGANISM: Artificial Sequence
<220> FEATURE:
<223> OTHER INFORMATION: Description of Artificial Sequence: Synthetic
      adaptor
<220> FEATURE:
<221> NAME/KEY: modified_base
<222> LOCATION: (43)..(49)
<223> OTHER INFORMATION: a, c, t, g, unknown or other

<400> SEQUENCE: 1
gagcaggtga ctctggcttc ctacacgacg ctcttccgat ctnnnnnnnc acccacactt       60
gacc                                                                   64

<210> SEQ ID NO 2
<211> LENGTH: 19
<212> TYPE: DNA
<213> ORGANISM: Artificial Sequence
```

<220> FEATURE:
<223> OTHER INFORMATION: Description of Artificial Sequence: Synthetic
      adaptor

<400> SEQUENCE: 2
aattggtcaa gtgtgggtg                                              19

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      L1_C primer

<400> SEQUENCE: 3
gggagatata cctaatgcta gatgacac                                    28

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      A_C primer

<400> SEQUENCE: 4
gagcaggtga ctctggctt                                              19

<210> SEQ ID NO 5
<211> LENGTH: 57
<212> TYPE: DNA
<213> ORGANISM: Artificial Sequence
<220> FEATURE:
<223> OTHER INFORMATION: Description of Artificial Sequence: Synthetic
      L1_N primer

<400> SEQUENCE: 5
gtgactggag ttcagacgtg tgctcttccg atcttgcaca tgtaccctaa aacttag    57

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      A_N primer

<400> SEQUENCE: 6
ctacacgacg ctcttccgat                                             20

<210> SEQ ID NO 7
<211> LENGTH: 52
<212> TYPE: DNA
<213> ORGANISM: Artificial Sequence
<220> FEATURE:
<223> OTHER INFORMATION: Description of Artificial Sequence: Synthetic
      NGS_F primer

<400> SEQUENCE: 7
caagcagaag acggcatacg agatcgtgat gtgactggag ttcagacgtg tg         52

<210> SEQ ID NO 8
<211> LENGTH: 58
<212> TYPE: DNA
<213> ORGANISM: Artificial Sequence
<220> FEATURE:

```
<223> OTHER INFORMATION: Description of Artificial Sequence: Synthetic
      NGS_R primer

<400> SEQUENCE: 8
aatgatacgg cgaccaccga gatctacact ctttccctac acgacgctct tccgatct        58

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      adaptor

<400> SEQUENCE: 9
gtcggtcaag tgtgggtg                                                    18

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tagcattggg agatatacct aatgctagat gacacatta                             39

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tgcacatgta ccctaaaact tagagtataa ta                                    32

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gatcggtcaa gtgtgggtg                                                   19

<210> SEQ ID NO 13
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gatctaccgt gatgaagggt ctcaggctct cctctctctc ttcatccgtt cagtctcttg      60
cacttcatat aaatgcctg                                                   79

<210> SEQ ID NO 14
<211> LENGTH: 79
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 14
gatctaccgt gatgaagggt ctcaggctct cctctctctc ttcatccgtt cagtctcttg      60
cacttcatat aaatgcctg                                                   79

<210> SEQ ID NO 15
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gatctaccgt gatgaagggt ctcaggctct cctctctctc ttcatccgtt cactctcttg      60
cacttcatat aaatgcctg                                                   79

<210> SEQ ID NO 16
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gatctaccgt gatgaagggt ctcaggctct cctctctctc ttcatccgtt cagtctcttg      60
cacttcatat aaatgcctg                                                   79

<210> SEQ ID NO 17
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gatctaccgt gatgaagggt ctcaggctct cctctctctc ttcatccgtt cagtctcttg      60
cacttcatat aaatgcctg                                                   79

<210> SEQ ID NO 18
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gatctaccgt gatgaagggt ctcaggctct cctctctctc ttcatccgtt cagtctcttg      60
cacttcatat aaatgcctg                                                   79

<210> SEQ ID NO 19
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 19
gatctaccgt gatgaagggt ctcaggctct cctctctctc ttcatccgtt cagtctcttg    60
cacttcatat aaatgcctg                                                 79

<210> SEQ ID NO 20
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gatctaccgt gatgaagggt ctcaggctct cctctctctc ttcatccgtt cagtctcttg    60
cacttcatat aaatgcctg                                                 79

<210> SEQ ID NO 21
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gatctaccgt gatgaagggt ctcaggctct cctctctctc ttcatccgtt cagtctcttg    60
cacttcatat aaatgcctg                                                 79

<210> SEQ ID NO 22
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gatctaccgt gatgaagggt ctcaggctct cctctctctc ttcatccgtt cagtctcttg    60
cacttcatat aaatgcctg                                                 79

<210> SEQ ID NO 23
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gatctaccgt gatgaagggt ctcaggctct cctctctctc ttcatccgtt cagtctcttg    60
cacttcatat aaatgcctg                                                 79

<210> SEQ ID NO 24
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gatctaccgt gatgaagggt ctcaggctct cctctctctc ttcatccgtt cagtctcttg    60
```
cacttcatat aaatgcctg                                                        79

<210> SEQ ID NO 25
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gatctaccgt gatgaagggt ctcaggctct cctctctctc ttcatccgtt cagtctcttg      60
cacttcatat aaatgcctg                                                        79

<210> SEQ ID NO 26
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gatctaccgt gatgaagggt ctcaggctct cctctctctc ttcatccgtt cagtctcttg      60
cacttcatat aaatgcctg                                                        79

<210> SEQ ID NO 27
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gatctaccgt gatgaagggt ctcaggctct cctctctctc ttcatccgtt cagtctcttg      60
cacttcatat aaatgcctg                                                        79

<210> SEQ ID NO 28
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gatctaccgt gatgaagggt ctcaggctct cctctctctc ttcatccgtt cagtctcttg      60
cacttcatat aaatgcctg                                                        79

<210> SEQ ID NO 29
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gatctaccgt gatgaagggt ctcaggctct cctctctctc ttcatccgtt cagtctcttg      60
cacttcatat aaatgcctg                                                        79

<210> SEQ ID NO 30

```
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gatctaccgt gatgaagggt ctcaggctct cctctctctc ttcatccgtt cagtctcttg     60
cacttcatat aaatgcctg                                                  79

<210> SEQ ID NO 31
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gatctaccgt gatgaagggt ctcaggctct cctctctctc ttcatccgtt cagtctcttg     60
cacttcatat aaatgcctg                                                  79

<210> SEQ ID NO 32
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gatctaccgt gatgaagggt ctcaggctct cctctctctc ttcatccgtt cagtctcttg     60
cacttcatat aaatgcctg                                                  79

<210> SEQ ID NO 33
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gatctaccgt gatgaagggt ctcaggctct cctctctctc ttcatccgtt cagtctcttg     60
cacttcatat aaatgcctg                                                  79

<210> SEQ ID NO 34
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gatctaccgt gatgaagggt ctcaggctct cctctctctc ttcatccgtt cggtctcttg     60
cacttcatat caatgcctg                                                  79

<210> SEQ ID NO 35
<211> LENGTH: 79
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 35
gatctaccgt gatgaagggt ctcaggctct cctctctctc tttatccgtt cagtctcttg      60
cacttcatat aaatgcctg                                                  79

<210> SEQ ID NO 36
<211> LENGTH: 74
<212> TYPE: DNA
<213> ORGANISM: Homo sapiens

<400> SEQUENCE: 36
gatcattttc accctcctct actactactt ccccctaactt cccctaattc cgtggtgcca    60
catcctgttc tcta                                                       74

<210> SEQ ID NO 37
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gatcattttc accctcctct actactactt ccccctaactt cccctaattc cgtgatgcca    60
catcctgttc tcta                                                       74

<210> SEQ ID NO 38
<211> LENGTH: 70
<212> TYPE: DNA
<213> ORGANISM: Homo sapiens

<400> SEQUENCE: 38
gatcctcctg ccctggcttc ccaaaatacc gggattatag ttgtgagcca ctgtgcttgg     60
cactcaaata                                                            70

<210> SEQ ID NO 39
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gatcctcctg ccctggcttc ccgaaatacc gggattatag ttgtgagcca ctgtgcttgg     60
cactcaaata                                                            70

<210> SEQ ID NO 40
<211> LENGTH: 74
<212> TYPE: DNA
<213> ORGANISM: Homo sapiens

<400> SEQUENCE: 40
gatctctctg cagaaaccct acaagccaga acagagtggg ggccaatatt caacattctt     60
aaagaaaaga attt                                                       74

<210> SEQ ID NO 41
<211> LENGTH: 74
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 41
gatctctctg cagaagccct acaagccaga acagagtggg ggccaatatt caacattctt      60
aaagaaaaga attt                                                        74

<210> SEQ ID NO 42
<211> LENGTH: 74
<212> TYPE: DNA
<213> ORGANISM: Homo sapiens

<400> SEQUENCE: 42
gatcctgact ataaggcagt caccactgta gaattaaggc atgtatgtac tgcatcctct      60
agaacagcac ctca                                                        74

<210> SEQ ID NO 43
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gatcctgact ataaggcagt caccactgta gaattaaggc atgtatgtac tgcgtcctct      60
agaacagcac ctca                                                        74

<210> SEQ ID NO 44
<211> LENGTH: 75
<212> TYPE: DNA
<213> ORGANISM: Homo sapiens

<400> SEQUENCE: 44
gatcaattat ttcataaaac aaaaatattc tttagtaatc cttattacca ccacctattt      60
tatatgtttt atata                                                       75

<210> SEQ ID NO 45
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gatcaattat ttcataaaac aaaaatattc tttagtaatc cttattacca ccacctattt      60
tatacgtttt atata                                                       75

<210> SEQ ID NO 46
<211> LENGTH: 48
<212> TYPE: DNA
<213> ORGANISM: Homo sapiens

<400> SEQUENCE: 46
gatcagcact tcactcaggg ccaacctttt ccccaggaag aaggaaat                   48

<210> SEQ ID NO 47
<211> LENGTH: 48
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 47
gatcagcact tcactcaggg ccaacctttt ccccgggaag aaggaaat                  48

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gtcggtcaag ggtgggtg                                                  18
```